United States Patent [19]

Droege

[11] Patent Number: 5,174,654
[45] Date of Patent: Dec. 29, 1992

[54] HEAT EXCHANGER EFFICIENCY MONITOR

[76] Inventor: Thomas F. Droege, 2 S. 942 Thornecrest La., Batavia, Ill. 60510

[21] Appl. No.: 852,309

[22] Filed: Mar. 18, 1992

[51] Int. Cl.$^5$ ............ G01N 25/00; G01N 25/18; G01N 25/20; G01K 17/00
[52] U.S. Cl. .................................. 374/7; 374/43; 165/11.1
[58] Field of Search ............ 374/6, 7, 43; 165/11.1, 165/11.2

[56] References Cited

U.S. PATENT DOCUMENTS

| | | | |
|---|---|---|---|
| 2,330,599 | 9/1943 | Kuehni | 374/44 |
| 2,951,360 | 9/1960 | Sampson et al. | 374/7 |
| 3,075,377 | 1/1963 | Lang | 374/43 |
| 3,724,267 | 4/1973 | Zoschak | 165/11.1 |
| 3,913,378 | 10/1975 | Hausler | 374/7 |
| 3,918,300 | 11/1975 | Weisstuch et al. | 374/7 |
| 4,024,751 | 5/1977 | Potrzebowski | 374/43 |
| 4,527,908 | 7/1985 | Arisi | 165/11.1 |
| 4,722,610 | 2/1988 | Levert et al. | 374/43 |

FOREIGN PATENT DOCUMENTS

| | | | |
|---|---|---|---|
| 0741126 | 6/1980 | U.S.S.R. | 374/43 |
| 855658 | 12/1960 | United Kingdom . | |
| 1403950 | 8/1975 | United Kingdom . | |
| 1423830 | 2/1976 | United Kingdom . | |

*Primary Examiner*—William A. Cuchlinski, Jr.
*Assistant Examiner*—Diego F. F. Gutierrez
*Attorney, Agent, or Firm*—Allegretti & Witcoff, Ltd.

[57] ABSTRACT

A monitor for measuring heat transfer resistance comprising a housing and one or more test block assemblies, each test block assembly includes a movable test block enclosed on two sides by parallel side supports and attached by a spring to a spring support. Each test block assembly is attached to the housing. The spring urges the movable test block away from the spring support. Additionally, the movable test block will contain a heater, a thermometer, or both the heater and a thermometer.

16 Claims, 3 Drawing Sheets

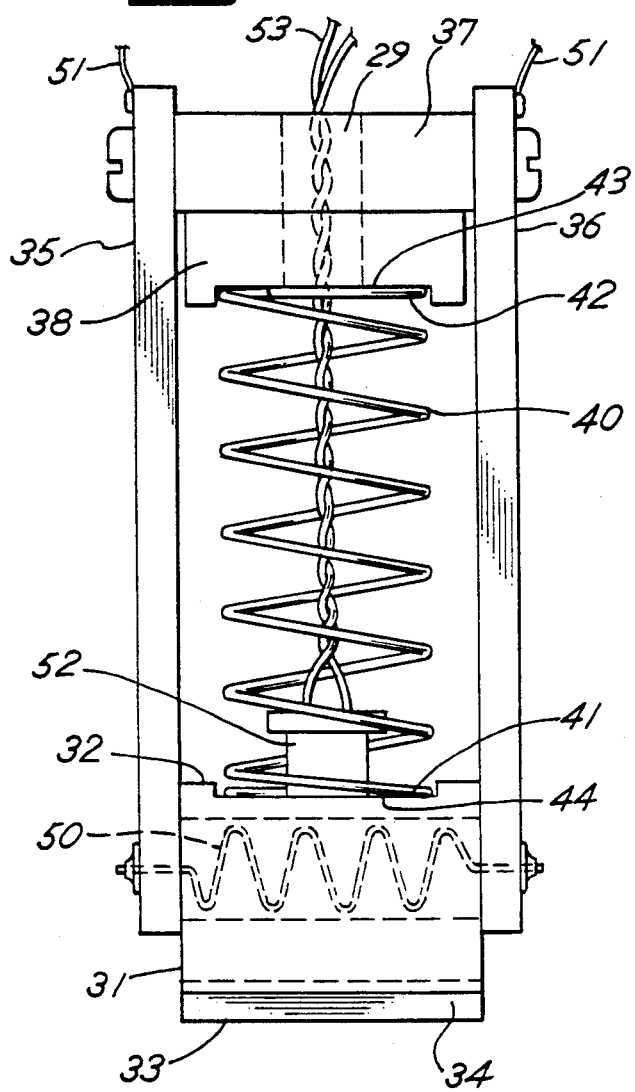
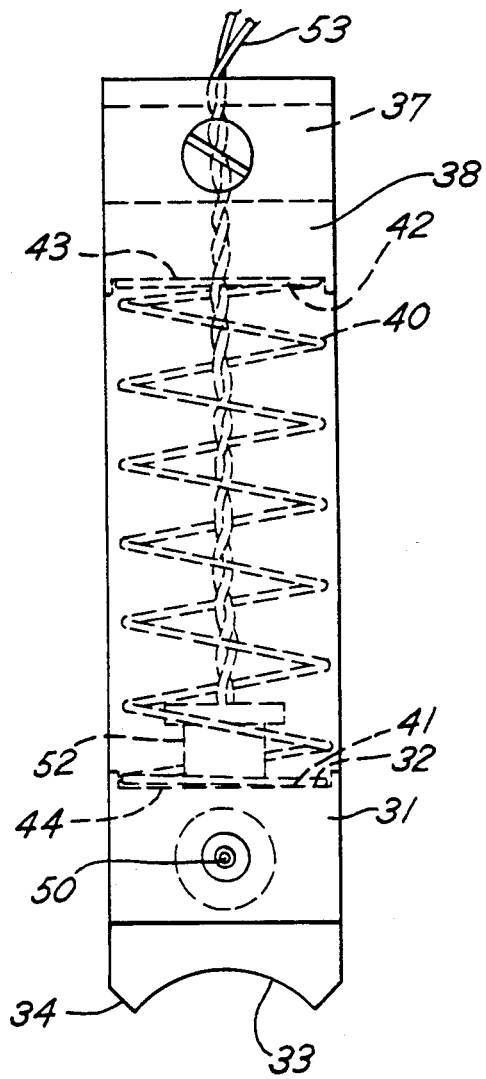
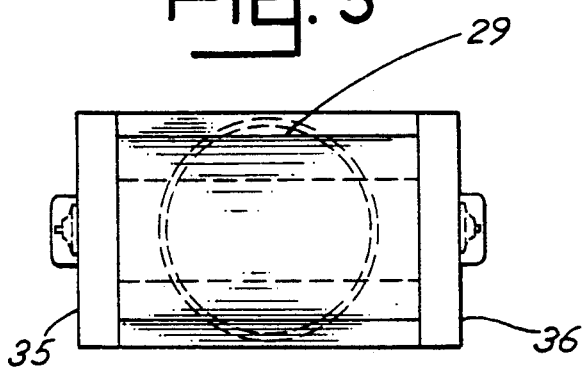

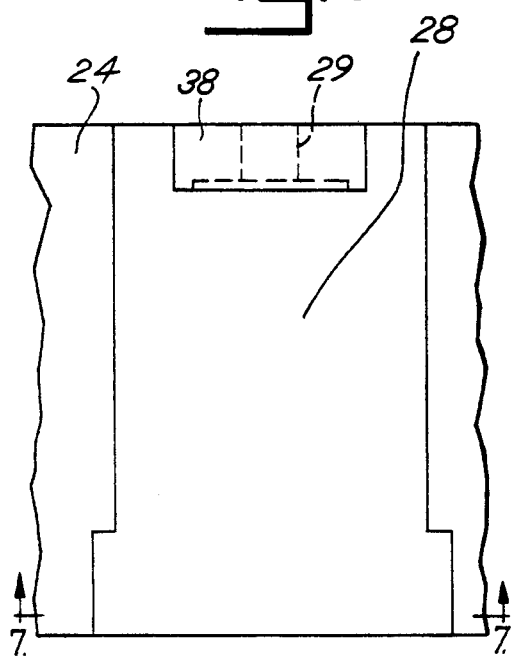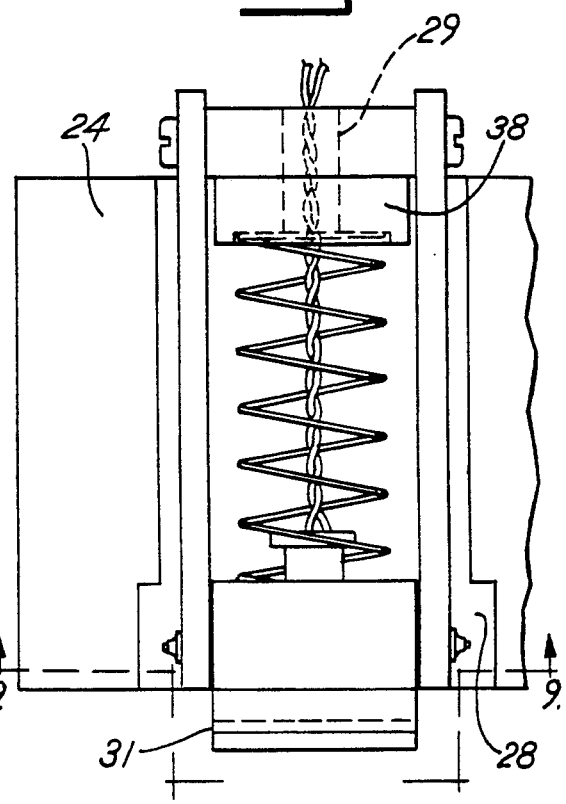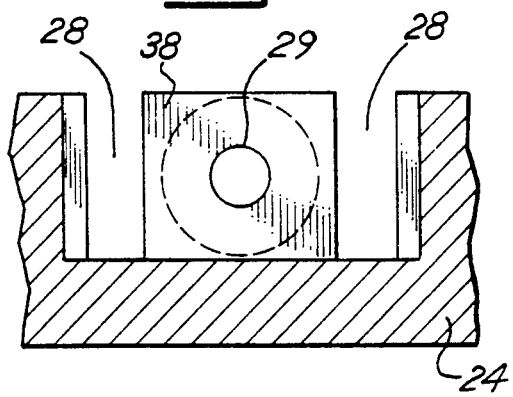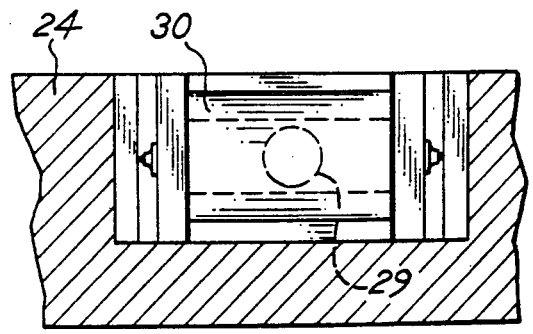

HEAT EXCHANGER EFFICIENCY MONITOR

BACKGROUND OF THE INVENTION

1. Field of the Invention

The present invention pertains to a portable apparatus useful in determining the thermal resistance of heat exchanger elements. The portable heat exchanger performance monitor is capable of being easily installed and removed from the simulated side arm of various types of heat exchangers thereby facilitating the evaluation of the heat exchanger fouling.

In thermodynamic apparatuses, such as heat exchangers, condensers, and the like, the formation of corrosion products, mineral, and organic deposits from various cooling media can, over time, impair the thermal transmission or thermal resistance of the heat exchanger elements. The formation of corrosion products, mineral deposits, and organic deposits can be counteracted by intermittently cleaning the heat exchanger or through the controlled addition of corrosion inhibiting additives to the heat exchange media. Cleaning the heat exchangers manually or by chemical addition can be very expensive. To reduce cleaning expenses, the heat exchanger tubes are monitored to establish the presence of and evaluate the magnitude of the build up of fouling materials. The cleaning or chemical addition can then be efficiently adjusted based on the magnitude of the fouling.

Apparatuses that monitor heat exchange fouling presently exist. However, the apparatuses presently used to evaluate heat exchanger tube fouling are bulky, dedicated devices which are difficult to maintain and expensive to operate.

2. Description of the Art

U.S. Pat. No. 2,330,599, to Kuehni, describes the basic principles for evaluating the thickness of a material using a thermal testing apparatus. The patent describes a thermal conductivity testing apparatus that includes a heat source and two resistance elements. One resistance element is placed into contact with a plate and the other is left uncontacted. The difference in the temperatures of the two resistance elements is monitored. The rate at which the temperature of the resistance monitor in contact with the plate decreases correlates to the thickness of the plate it touches.

Other patents also describe this method of measuring the thermal conductivity of fluids and other materials. These patents include United Kingdom Patents 1,423,830, 1,403,950, and 855,658. The '658 patent describes an apparatus for measuring the thermal conductivity of a test material using two probes mounted within an insulated block where one probe is contacted with the test material while the other probe remains isolated from the test material. The '830 patent describes an apparatus and method for measuring heat flux using a single probe. A single probe is exposed to a heat flux and the rate at which the probe increases in temperature is measured. The '950 patent describes a method for measuring the thermal diffusivity of a sample by exposing a first surface of the sample to heat or radiation source while maintaining a second surface of a sample at a constant temperature. When the first surface is exposed to a heat or radiation pulse, the power necessary to maintain the second surface of the sample at the desired temperature is reduced. The power consumption then can be correlated with the heat or radiation pulse magnitude to determine the thermal diffusivity of the sample.

U.S. Pat. No. 4,024,751 describes an apparatus for determining the heat transfer efficiency of a heat exchanger wall. The '751 patent recognizes that the efficiency of a heat exchanger is diminished by build up of materials and scale on heat exchanger wall surfaces. The claimed apparatus evaluates the magnitude of scale build up by heating the wall of a heat exchanger tube from first pre-determined temperature to a second pre-determined temperature, halting the heating, and measuring the time it takes for the temperature of the measured portion of the heat exchanger to drop from the second predetermined temperature to the first predetermined temperature. The amount of time it takes to return from the second temperature to about the first temperature can be correlated to heat exchanger scale build up. The apparatus disclosed is a permanent apparatus including a heating means in direct contact with a heat exchanger tube.

U.S. Pat. No. 4,722,610 describes a monitor for determining the build up of slag on the flame side of water cooled walls of a coal-fired steam generator. The monitor includes a heater located adjacent to a thermocouple in a body. The thermocouple usually monitors the temperature of the body and when the body temperature decreases, this is an indication of slag build up. This indication is confirmed by heating the body with the heater, and measuring the temperature drop of the body using the same thermocouple. A slow drop in the temperature of the body indicates a large build up of slag.

Other apparatuses and methods for evaluating heat exchanger performance are known. However, the art lacks methods or apparatuses that utilize a portable monitor that is able to measure the performance of heat exchangers.

SUMMARY OF THE INVENTION

A principal object of this invention is to provide a monitor for measuring heat exchanger performance. The monitor is compact in size so that it is easily portable and is attached and detached from heat exchanger test tubes.

This invention relates generally to a portable monitor comprising a housing and one or more test block assemblies. The housing includes a box having two opposing apertures complementary to a test tube, and a box cover. Each test block assembly includes a movable test block, a spring, a spring stop and parallel side supports. The movable test block is located between the parallel side supports. The spring support is fixedly attached to the parallel side supports. The spring unites the movable test block with the spring support and urges the movable test block away from the spring support.

Further, the portable monitor of this invention comprises a housing and two or more test block assemblies. The housing includes a box having two opposing apertures complementary to a test tube, and a box cover. Each test block assembly is enclosed by and fixedly attached to the housing. Each test block assembly includes a movable test block having a concave face, two parallel circuit boards, a spring, and a spring stop. The movable test block is located between the parallel circuit boards. The spring stop is fixedly located between the parallel circuit boards. The spring unites the fixed spring stop with the flat face of a movable test block. The spring biases the concave face of the movable test block away from the spring support. Additionally each test block may include a thermometer, a heater, or both a thermometer and a heater. Finally, this invention contemplates a portable monitor having two or more test block assemblies located in a housing adjacent to one another, or in opposition to one another.

DESCRIPTION OF THE DRAWINGS

There is shown in the drawings a presently preferred embodiment of the invention wherein like numerals in the various figures pertain to like elements and wherein;

FIG. 3 is a front view of a test block assembly of this invention;

FIG. 4 is a side view of the test block assembly of this invention;

FIG. 5 is a top view of the test block assembly of this invention;

FIG. 6 and FIG. 7 are front and top views respectively of a support block of the portable monitor of this invention; and FIG. 8 and FIG. 9 are front and top views respectively of a support block including a moveable test block assembly of this invention.

DESCRIPTION OF THE CURRENT EMBODIMENTS

The present invention relates to an improved portable monitor that is capable of monitoring heat exchanger efficiency. The portable monitor of this invention is compact in size. Additionally, a preferred portable monitor of this invention is capable of performing multiple heat transfer resistance measurements under a variety of conditions in a compact space. The portable monitor of this invention is better understood by to FIGS. 1 through 9 which show various aspects of a preferred portable monitor of this invention.

Figure 1:
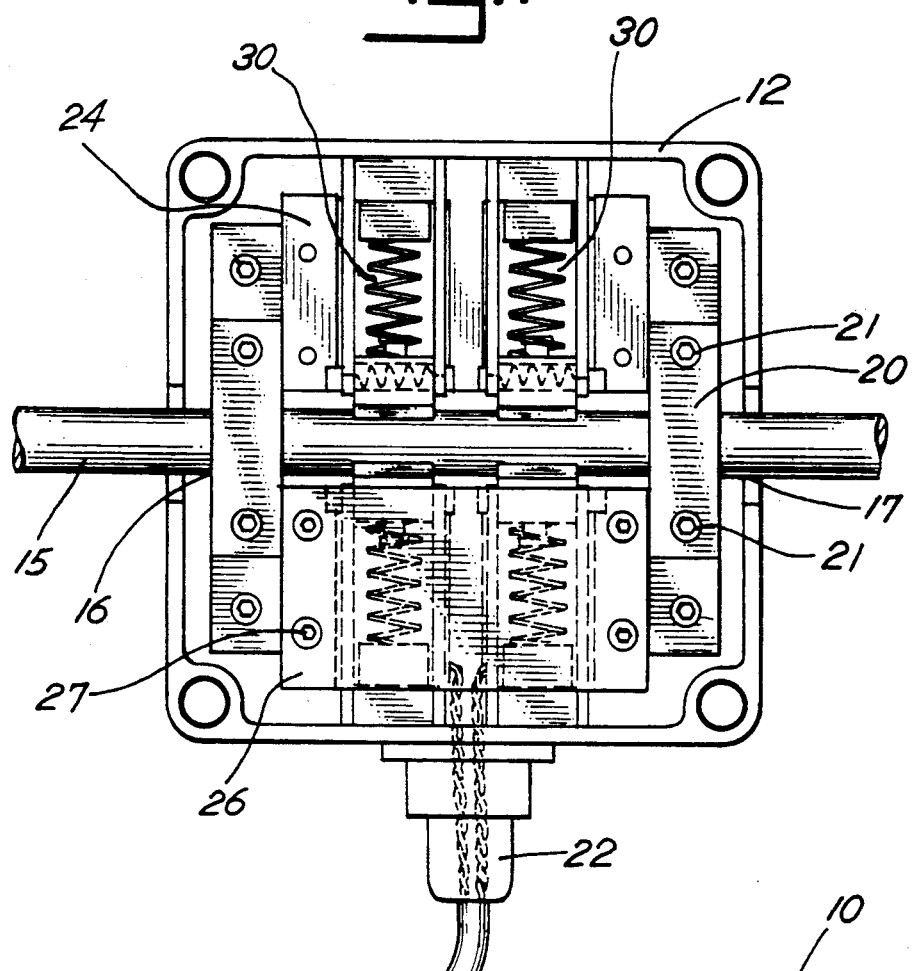
FIG. 1 is a top view of the portable monitor of this invention.
Figure 2:
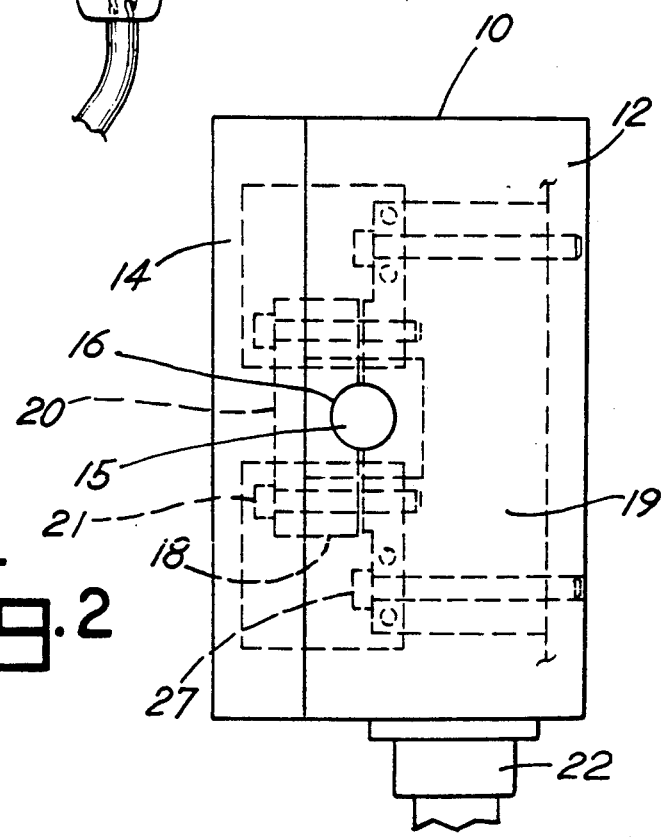
FIG. 2 is a side view of the portable monitor of this invention.

FIGS. 1 and 2 show top and side views respectively of the portable monitor of this invention. The portable monitor includes housing 10 comprising box 12 and box cover 14. FIG. 1, the top view of the portable monitor, shows the housing 10 with box cover 14 removed so that the contents of the housing are exposed. Housing 10 includes a first aperture 16 and a second aperture 17. The apertures may be located in box 12 or the box cover 14 or in both.

First aperture 16 and second aperture 17 are located on opposite sides of housing 10 and provide a location where a test tube 15 can pass through housing 10 unimpeded. A test tube 15 is a standard feature on many heat exchangers. Test tube 15 mimics conditions occurring in the tubes contained in a multi-tube heat exchanger. The conditions that are mimicked include fluid temperature, fluid flow rate, fluid composition, and fluid pressure. Instead of being located in the heat exchanger, however, test tube 15 is located outside of the heat exchanger.

Housing 10 also includes a test tube support brackets 18 complementary to both first aperture 16 and to second aperture 17 for coupling the portable monitor of this invention to test tube 15. Each test tube support bracket 18 includes a first bracket 19 which is fixedly attached to housing 10 and second bracket 20 which is attached by fasteners 21 to first bracket 19. First bracket 19 and second bracket 20 include depressions complementary to the geometry of test tube 15. Typically test tube 15 is circular and the depressions in first bracket 19 and second bracket 20 are concave.

An electrical connector 22 is also integral to housing 10. Electrical connector 22 electrically links heaters, thermometers, and other electrical devices in housing 10 to a source of electricity or to temperature or heater displays and controls outside of housing 10.

The purpose of housing 10 is to protect the test block assemblies 30 enclosed by the housing from the external environment. Housing 10 protects the test block assemblies 30 from tampering, from spills, and from other hazards that could potentially damage test block assemblies or that could affect the accuracy of the data collected from the monitor. Housing 10 can be purged with an inert gas if the portable monitor is located in an area that might be prone to explosions. Additionally, the purge gas can be kept at a constant temperature in order to insulate the test block assemblies from air currents which can disturb measurements.

One or more test block assemblies 30 are located in support block 24 which attached to housing 10 by fasteners 27. Referring now to FIGS. 3-5, each test block assembly 30 includes a movable test block 31 having a flat face 32 and a concave face 33. Movable test block 31 is located between parallel side supports which include a first side support 35 and a second support side 36. The parallel side supports fixedly attached to beam 37. Beam 37 separates the parallel side supports and helps to maintain in the parallel side supports in a parallel position. A support block spring support 38 is integral to support block 24. Support block spring support 38 which also acts as a spring stop includes first depression 43. Moveable test block 31 includes a second depression 44 in flat face 32.

A spring 40 is located at first end 41 in second depression 44 in flat face 32. A second end 42 of spring 40 is located in first depression 43 of support 38. First depression 43 and second depression 44 are both shallow to allow spring 40 to be easily installed and removed from the depressions. The spring 40 urges movable test block away from spring support 38. The tension and size of spring 40 and the depth of first depression 43 and second depression 44 are selected so that spring 40 will urge moveable test block 31 slightly beyond the test block assembly side supports and into the channel that will eventually be occupied by test tube 15. A moveable test block 31 that occupies only a small portion of the test tube channel can be easily "snapped" into place into contact with test tube 15 and into support block 24.

Each test block assembly 30, is capable of being totally removed from and replaced in housing 10. Test block assembly 30 is not attached to housing 10. Instead test block assembly is reversibly positioned in a test block assembly site 28 machined into support block 24. When located in a test block assembly site 28 test block assembly 30 freely floats in support block 24. The "free floating" aspect of moveable test block 31 is important. Moveable test block 31 aligns with test tube 15 so the entire concave face 33 is contacts test tube 15. By designing movable test block 31 with a very sloppy fit onto test tube 15 this is accomplished. Use of terminal grease between test tube 15 and moveable test block 31 is desirable to make good uniform contact.

First side support 35 and second side support 36 are manufactured of a thin rigid material. The side supports act to guide the movement of movable test block 31. The side supports prevent movable test block 31 from moving laterally in relation to test tube 15. The combination of support block cover 26 fixedly attached by fasteners 27 to support block 24 also acts to guide the movement of moveable test block 31. Together the four pieces box in moveable test block 31 so that it can only move towards and away from test tube 15.

It is preferred that first side support 35 and second side support 36 are made of circuit board materials and are in fact themselves printed circuit boards. When the parallel side supports are circuit boards, they may include printed circuits for electronically uniting contact 54 of heater 50 or thermometer 52 or both, to heater leads 51 and thermometer lead 53 respectively. The heater leads 51 and thermometer leads 53 then pass into electrical connector 22 which protects the heater and thermometer leads outside of housing 10, and which unites the heater and thermometer leads with source of electricity and/or monitoring devices.

Alternately, the electrical connection to heater 50 and the lead to thermometer 52 can pass through hole 29 through beam 37 and support block spring support 38 before passing into electric connection 22. FIGS. 3-5 depict an installed test block assembly 30 with thermometer lead 53 passing through hole 29.

Movable test block 31 has a concave face 33 opposite flat face 32. Concave face 33 contacts test tube 15 such that essentially the entire concave face 33 of movable test block 31 contacts a complementary convex surface of test tube 15. Moveable test block 31 also has a bevel 34 along the long front and back lengths of concave face 33. Bevel 34 allows the moveable test block 31 to be easily associated with test tube 15.

It is possible that test tube 15 will have a non-circular cross-section. In such a situation, the movable test block will not have a concave face but will have a face that is complementary to the geometry of test tube 15. However, it is preferred that test tube 15 have a circular cross-section and, as a result, movable test block 31 will have a concave face 33.

The movable test block serves at least two purposes. The movable test block is made of a thermally conductive material that can be quickly heated to a desired controlled temperature. The movable test block also must remain in intimate contact with test tube 15 in order to measure the ability of test tube 15 to remove heat from movable test block 31. The conductive nature of movable test block 31 along with the fact that it is in intimate contact with test tube 15 ensures that the movable test block 31 will, except when heated, be at a temperature essentially identical to the temperature of the fluid in test tube 15.

Movable test block 31 can be made from any known conductive material. The conductivity and the thermal capacity of moveable test block 31 are both important for a fast thermal response. The best conductive materials are metals including silver, gold, copper, and aluminum in that order. Silver has been found to be twice as efficient as the next practical candidate, copper. The preferred conductive material therefore, is silver.

Movable test block 31 may include a heater 50, a thermometer 52, or both a heater and a thermometer. A preferred heater 50 is a resistance type heater which is generally located in a hole drilled through movable test block 31 parallel to test tube 15. Heater 50 is preferably attached by a contact to a printed circuit board side support. The printed circuit board electrically unites heater 50 with heater lead 51. Heater leads 51 then exist housing 10 via electrical connector 22.

Movable test block 31 may also include a thermometer 52. Thermometer 52 may be a transistor or a thermistor. A preferred thermometer is a solid state semi-conductor transistor Model AD-590 manufactured by Analog Devices. Thermometer 52 is typically attached to flat face 32 of movable test block 31. Alternately, thermometer 52 may be mounted in a small hole in moveable test block 31. A thermometer lead 53 may unite thermometer 52 with a circuit board acting as a parallel side support. Alternately, thermometer lead 53 can pass through the center of spring 40 and through hole 29 and run directly to electrical connector 22.

The portable monitor of this invention is attached to test tube 15 to monitor the efficiency of an associated heat exchanger. In order to attach the portable monitor to a test tube, box cover 14 must be removed from housing 10 to expose the inside of box 12. Fasteners 21, uniting first bracket 19 with second bracket 20 are removed and first bracket 19 is detached from test tube support bracket 18. Box 12 is oriented such that test tube 15 rests on the concave face of second support 20. Housing 10 is then secured to test tube 15 by securing first bracket 19 to second bracket 20 with fasteners 21.

Test block assemblies 30 can now be placed into contact with test tube 15. Referring to FIGS. 6-9, one or more support blocks 24 are located in housing 10. Each support block 24 includes one or more test block assembly recesses 28. Test block assembly recess 28 may be totally empty or it may include a test block assembly 30 without spring 40 and without moveable test block 31. Generally a test block assembly 30 without a spring 40 or moveable test block 31 will be partially placed in test block assembly recess 28. Spring 40 will be placed between support block spring support 38 and moveable test block 31 and the entire test block assembly will be slip fit into test block assembly recess 28 so that moveable test block 31 contacts test tube 15. When each concave face 33 of each movable test block 31 is contacting test tube 15, a support block cover 26 is attached to support block 24 to cover all test block assemblies. Box cover 14 is finally attached to box 12 to define housing 10.

The assembled and mounted portable monitor can now be used to evaluate the efficiency of the heat exchanger associated with test tube 15. The efficiency of the heat exchanger is directly related to the cleanliness of the heat exchanger tubes. Test tube 15 mimics the extent of any fouling present in the heat exchange tubes. To evaluate the efficiency of test tube 15, heater 50, in a movable test block 31 is heated until movable test block 31 reaches a temperature above that of the fluid in test tube 15. Once movable test block 31 reaches a desired temperature, the heating is discontinued and movable test block 31 is allowed to cool until it reaches a second predetermined temperature above that of the fluid in test tube 15. The rate cooling of movable test block 31 corresponds to the cleanliness of test tube 15. If test tube 15 is clean, then movable test block 31 will cool at rate slightly faster than the cooling rate of movable test block 31 when it contacts a fouled test tube.

It is clearly important that the rate of change of the temperature of movable test block 31 be monitored. This can be accomplished using an external recording device. The temperature, data obtained from the portable monitor can be used to adjust chemicals used to prevent tube fouling, or it can be used as a basis for determining when the heat exchanger should be manually cleaned.

The portable monitor of this invention may include a single test block assembly 30 having movable test block 31 which includes a heater 50 and a thermometer 52. It is preferred, however, that the portable monitor of this invention include two or more test block assemblies 30. When two or more test block assemblies are employed, at least one movable test block will include both a heater 50 and thermometer 52. Other adjacent movable test blocks can contain a thermometer 52, or a heater 50 or a combination thereof.

The description above has been offered for illustrative purposes only, and it is not intended to limit the scope of the invention of this application which is defined in the following claims.

What I claim is:

1. A heat exchanger efficiency monitor comprising a housing including two opposing apertures complementary to a heat exchanger test tube, at least one test block assembly located in the housing and an electrical connector integral to said housing, each test block assembly including two parallel side supports, a moveable test block located between the two parallel side supports, a beam uniting the two parallel side supports, a spring contacting the moveable test block and a spring stop, the moveable test block including a thermometer and a heater united with the electrical connector.

2. The monitor of claim 1 wherein the heater is an electric resistance heater.

3. The monitor of claim 1 wherein the thermometer is transistor or a thermistor.

4. The monitor of claim 1 wherein each movable test block has a concave face complementary to the convex dimension of the heat exchanger test tube.

5. The monitor of claim 1 wherein the two parallel side supports are each circuit boards.

6. The monitor of claim 5 wherein the circuit boards electrically unite the thermometer or the heater or both with the electrical connector.

7. The monitor of claim 1 wherein the housing includes at least two test block assemblies.

8. A heat exchanger efficiency monitor for making multiple simultaneous heat transfer resistance measurements comprising a compact housing including a box having two opposing apertures complementary to a test tube, a box cover, and at least two test block assemblies located within the housing and fitting into a support block associated with the housing, each test block assembly including a moveable test block having a flat face and a concave face, the moveable test block located between parallel circuit boards united by a beam, a spring contacts a spring stop integral to the support block and the flat face of the moveable test block urging the concave face of the moveable test block away from the spring stop, at least a first moveable test block further including a thermometer and at least a second moveable test block further including a heater, the thermometer and the heater electrically united with an electrical connector integral to the housing.

9. The monitor of claim 8 having two opposing test block assemblies.

10. The monitor of claim 8 having two pairs of opposing test block assemblies.

11. The monitor of claim 8 wherein the movable test blocks are made of silver.

12. The monitor of claim 8 wherein the heater is an electric resistance heater.

13. The monitor of claim 8 wherein the thermometer is a transistor or a thermistor.

14. The monitor of claim 8 wherein the parallel circuit boards unite the heater with the electrical connector.

15. The monitor of claim 8 whereas a thermometer lead wire electrically unites the thermometer with the electrical connector.

16. A portable monitor for making multiple simultaneous heat transfer resistance measurements comprising:

a housing including a box, a box cover, an electrical connector integral to the box, and a support block attached to the housing including four test block assembly recesses;

a plurality of test block assemblies, each test block assembly complementary to a test block assembly recess and including a moveable test block having a convex face and a flat face, each moveable test block slidably located between parallel printed circuit boards that are united by a beam, and a spring contacting a spring stop and the flat face of the moveable test block, each moveable test block including a heater and a thermometer electrically united to the electrical connector; and a support block cover.

* * * * *